United States Patent [19]

Anderson

[11] Patent Number: 5,051,872
[45] Date of Patent: Sep. 24, 1991

[54] HEMISPHERICAL NON-GLARE ILLUMINATOR

[75] Inventor: Charles H. Anderson, Dallas, Tex.

[73] Assignee: Texas Instruments Incorporated, Dallas, Tex.

[21] Appl. No.: 524,684

[22] Filed: May 15, 1990

Related U.S. Application Data

[63] Continuation of Ser. No. 221,159, Jul. 19, 1988, abandoned.

[51] Int. Cl.$^5$ .............................................. F21V 7/04
[52] U.S. Cl. ..................................... 362/32; 362/335; 362/355; 362/268; 362/331
[58] Field of Search ................... 358/101, 106, 107; 362/32, 307, 311, 335, 361, 328, 336, 351, 355, 17, 89, 268, 300, 331

[56] References Cited

U.S. PATENT DOCUMENTS

| | | | |
|---|---|---|---|
| 1,953,299 | 4/1934 | Grant | 362/89 |
| 3,971,621 | 7/1976 | Albrecht-Buehler | 362/32 X |
| 4,266,534 | 5/1981 | Ogawa | 362/336 X |
| 4,428,673 | 1/1984 | Yoshida | 362/355 X |
| 4,455,592 | 6/1984 | Martino | 362/355 X |
| 4,460,940 | 7/1984 | Mori | 362/307 X |
| 4,635,111 | 1/1987 | Moore | 358/106 |
| 4,677,473 | 6/1987 | Okamoto et al. | 362/32 X |
| 4,677,531 | 6/1987 | Szeles | 362/32 |
| 4,882,492 | 11/1989 | Schlager | 358/101 X |
| 4,947,030 | 8/1990 | Takahashi | 362/268 |
| 4,974,919 | 12/1990 | Muraki et al. | 362/268 |

Primary Examiner—Ira S. Lazarus
Assistant Examiner—Sue Hagarman
Attorney, Agent, or Firm—B. Peter Barndt; James T. Comfort; Melvin Sharp

[57] ABSTRACT

A translucent hemispherical diffuser provides shadowless, uniform illumination of an object to be inspected or otherwise viewed. The optical medium of the translucent diffuser has a milk glass optical consistency, and/or one or more surfaces of the diffuser may be textured to diffuse light entering or leaving the optical medium of the diffuser. The hemispherical diffuser is placed between a light source and the object to be viewed. Light from the light source entering the optical medium of the diffuser is re-radiated uniformly from the concave surface of the diffuser. The object to be viewed is located approximately at the center of curvature of the hemispherical diffuser. Thus, the radiating concave surface of the diffuser subtends a solid angle of approximately two -pi steradians. Light may be scattered and diffused by various reflecting surfaces external to the diffuser, prior to entering the optical medium of the diffuser. One embodiment of the diffuser includes reflecting surfaces as an integral part of the diffuser. Light sources may be remote lamp and fiber optical systems, or local, spirally wound neon tubes covering the diffuser. Each diffuser includes a viewing port for observing the illuminated object. The viewing port may have associated with it a beam splitter or half silvered mirror assembly to direct light toward the object to prevent an image of the port from being reflected by the object, and to pass light reflected by the object to a video camera or other viewing device.

26 Claims, 8 Drawing Sheets

HEMISPHERICAL NON-GLARE ILLUMINATOR

This is a continuation of application Ser. No. 221,159, filed July 19, 1988, now abandoned.

BACKGROUND OF THE INVENTION

1. Field of the Invention

This invention relates to illumination systems for visual inspection systems, and more particularly, it relates to apparatus and methods for hemispherical or shadowless illumination of an object to be inspected visually.

2. Description of the Related Art

Machine vision and visual inspection have faced significant limitations in applications involving viewing of highly reflective objects. Examples include: solder joints, electrical component leads, and machined or brightly finished metal objects.

The solid state or tube-type sensors, such as TV or video cameras, typically used for imaging in machine vision systems, tend to saturate or bloom when viewing objects having areas of extremely bright specular reflections, or hot spots, produced by conventional sources of illumination. These saturated hot spots of the image of the object being viewed, preclude observation of details in those areas of the image, and may mask adjacent areas as well.

"Specular reflections" are mirror-like reflections from highly polished or shiny objects with areas of smooth surface. Typically, in machine vision systems, such reflections can occur when metal, or highly polished objects, or objects with areas of smooth surface reflect light from a concentrated light source.

"Saturation" refers to the condition in which a video camera's output is at maximum peak-to-peak voltage, and can deliver no more. The dynamic range of video cameras frequently is insufficient to accommodate the excessive dynamic range of objects having bright or highly reflective areas on their surfaces, when the camera is adjusted for the best picture on normal image detail. Typically, such saturated areas of the picture will spread or enlarge in size due to the overloaded condition. This spreading is called "blooming". The saturated and bloomed portions of the image may obscure key areas of interest in the image. "Dynamic range" refers to the range of reflected light intensity, from brightest to darkest, of an illuminated object or its visual image.

Similarly, with visual inspection systems utilizing microscopes, image hot spots cause problems of human eye fatigue during manual visual inspection, and cause exposure problems when photographs are taken through the microscope. That is, due to problems associated with the limited dynamic range of photographic film, and reciprocity failure, visual hot spots may be over-exposed if the exposure time is calculated for correct exposure of non-hot-spot areas of the image. Likewise, non-hot-spot areas may be under-exposed if the exposure time is calculated for correct exposure of the hot spot areas of the image.

Conventional sources of illumination for visual inspection systems, include: incandescent illuminators, ringed arrays of lamps, light emitting diodes, focused filament projectors, straight and circular fiber optics light sources, and varied sizes and types of gas-filled and fluorescent lamps. These conventional sources of illumination all produce visual hot spots due to the fact that they present to the object under illumination, concentrated sources of light. For example, an annulus of glass or plastic fibers often is used as a means of conducting light from a remote lamp or other light source. However, such a fiber optics annulus provides diffuse illumination only over small solid angles, and thus, still constitutes a concentrated source of light. The solid angle is measured from a vertex at the location of the object under illumination.

Therefore, a need was felt to develop an illumination system having an extremely diffuse illumination pattern over a large solid angle, to eliminate or minimize the occurrence of bright reflections, or hot spots, from objects having areas of high reflectivity on their surfaces. Such a system would produce reflected light patterns having reduced dynamic ranges.

Figure 1:
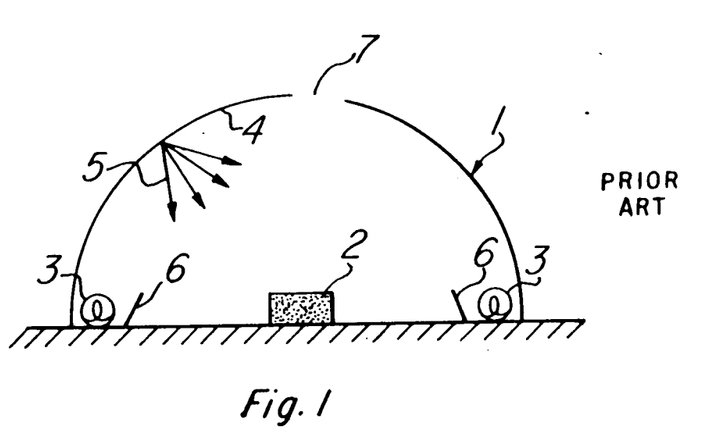
FIG. 1 is a side sectional view of a prior art illumination system with a hemispherical reflector.

A prior art attempt to provide a source of diffuse light over a large solid angle, is described in "AUTOMATED VISUAL INSPECTION", page 105, IFS (Publications) Ltd, United Kingdom, and is illustrated in FIG. 1. Turning now to FIG. 1, a hemispherical reflector 1 covers an object-under-examination 2. The source of illumination is a circular lamp 3 which directs light against the inner surface 4 of the hemispherical reflector 1. The light from the circular lamp 3 is scattered by the inner surface 4, as scattered light 5. Presumably, some of the scattered light 5 strikes the object-under-examination 2. The inner surface 4 is painted matt white or stippled inside to accomplish the scattering of the light. A lamp reflector 6 is disposed between the object-under-examination 2 and the circular lamp 3. The camera opening 7 in the top of the hemispherical reflector 1 allows a camera to view and to form an image of the object-under-examination 2.

One disadvantage of the prior art hemispherical reflector is that the only diffusing element, the hemispherical reflector 1, works by reflection. Thus, all light sources must be located and all diffusion must take place within the interior of the hemispherical reflector 1. Among other things, this results in too bulky a device in such cases as where an illuminator is required to fit in a small space, such as on a microscope, or on optical inspection equipment on a production line. Also, with the light source in the hemispherical reflector 1, it is required that electric wiring be conducted to the reflector, which might be undesirable in certain situations where the presence of electrical power is undesirable. If problems develop with the circular lamp 3, it is necessary that maintenance be carried out upon the hemispheric reflector, possibly requiring the removal of the reflector from the optical system of which it may be a part. The location of the circular lamp 3 limits the choice of possible lamp types, for instance, size constraints would prevent the use of high intensity incandescent lamps.

Another disadvantage is that the hemispherical reflector is the only diffusing element.

A further disadvantage is that the lamp reflector 6 reduces the size of the solid angle subtended by the area from which diffuse light emanates.

SUMMARY OF THE INVENTION

One embodiment of the invention provides for a translucent, hemispherical diffuser, having a convex surface and a concave surface, which absorbs light incident upon its convex surface, and emits the light diffusely from its concave surface. An object to be inspected or examined is located on the concave side of the diffuser, so that the light diffusely emitted by the diffuser, strikes the side of the object facing the diffuser, from many angles. Light is directed to be incident upon virtually all of the convex surface of the diffuser, thus, diffuse light is emitted by substantially all of the concave surface. The object is located near the center of curvature of the concave surface of the diffuser, therefore, the diffusely emitted light rays strike and illuminate the object at a solid angle of substantially two-pi steradians (that is, a "180 degree" solid angle). Each embodiment of the invention includes a viewing port for viewing the illuminated object. The viewing port may be located axially in the center of the hemispherical diffuser, or it may be off-axis to view the illuminated object from an oblique angle.

Several embodiments of the hemispherical diffuser include a lamp remote from the hemispherical diffuser. In these embodiments, light may be conducted from the lamp by a fiber optical cable, to be emitted toward the convex surface of the diffuser.

One of these embodiments includes a negative diverging lens and a conical shaped reflector for diffusing the light emitted by the fiber optical cable, before it is incident upon the convex surface of the diffuser. In this embodiment, an off-axis viewing port is provided to one side of the negative diverging lens.

In another of these embodiments, two conical shaped reflectors are used for diffusing the light emitted by the fiber optical cable. The negative diverging lens is not used in this embodiment, to allow on-axis viewing of the illuminated object.

A further embodiment of the invention includes a remote lamp and a fiber optical cable to conduct light from the lamp to the hemispherical diffuser. The hemispherical diffuser is translucent and has a concave surface and an opposed flat surface. The fiber optical cable terminates in a fiber optics ring which is attached to the flat surface of the diffuser. Light emitted by the fiber optics ring enters the flat surface of the diffuser and reflected and re-reflected within the optical medium of the diffuser, and is then emitted from the concave surface, generally directed toward the object to be illuminated. A stage of light diffusion occurs when the light is reflected and re-reflected within the optical medium of the diffuser. A further stage of diffusion may occur when the light is emitted from the concave surface of the diffuser.

The foregoing embodiments of the invention solve some of the previously referred to problems of the prior art hemispherical reflector, by locating the lamp remotely from the diffuser. In this manner, the physical size of the diffuser assembly can be minimized, making it easier to utilize the diffuser assembly on relatively small optical systems such as microscopes and small video cameras, such as CCD cameras. There is no requirement for wires running to the diffuser assembly, and high intensity lamps can be used which would be too large or bulky if they could not be located remotely from the diffuser assembly. Also, there is no limitation as to the shape of the lamp. The prior art lamp must be circular in shape, as indicated in FIG. 1. The remotely located lamp of the invention allows lamps to be changed and maintenance performed on the lamp assembly without having to disturb or remove the diffuser assembly. In addition, the translucent diffuser permits the lamp to be located remotely by allowing the light source to come from the convex side of the diffuser, which is the side of the diffuser opposite the object to be illuminated.

Another embodiment of the invention includes a gas-discharge light source spirally wound generally in a hemispherical shape, so that a translucent, hemispherical diffuser can be placed within the space defined by the concave surface of the hemispherical light source. That is, the spiral light source is disposed about the convex surface of the diffuser, to supply an even source of light to substantially the entire area of the convex surface of the diffuser. The diffuser further diffuses the light and emits the diffused light from the concave surface of the diffuser. The object to be illuminated is positioned generally at the center of curvature of the concave surface of the diffuser. This embodiment includes a view port centered in the axial region of the diffuser.

The spiral light source and the diffuser generally may have a hemispherical shape or may have a flattened hemispherical shape, wherein the axially central portion of the light source and diffuser are flattened. This embodiment of the invention may include a hemispherically shaped reflector covering the spiral light source to aid in reflecting and scattering light back toward the light source and therefore toward the diffuser. Alternatively, the reflector may be omitted.

The translucent diffuser permits the light source to be located on the convex side of the diffuser, which is the side of the diffuser opposite the side facing the object to be illuminated. This allows more freedom in placement of the light source since what happens on the convex side of the diffuser is less likely to interfere with or get between the diffuser and the object to be illuminated.

The translucent diffuser allows several stages of diffusion to occur prior to the light reaching the concave surface of the diffuser. For instance, various reflectors or spiral lamps can be used to provide a source of light to the diffuser which is already diffused.

These and other advantages will become more apparent in the following description.

DESCRIPTION OF THE PREFERRED EMBODIMENTS

Figure 2A:
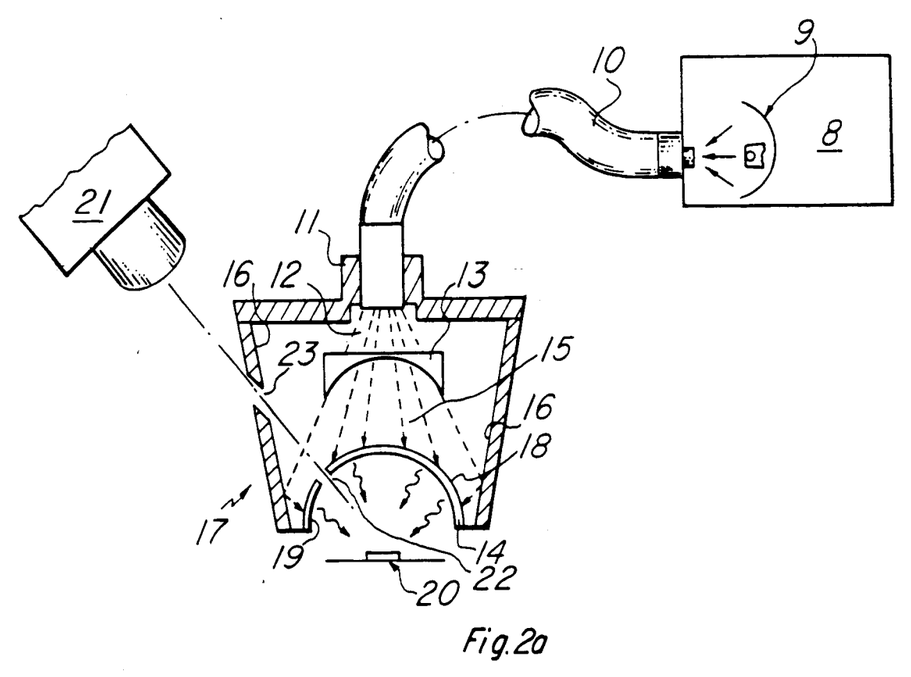
FIG. 2A is a side sectional view of an embodiment of the invention with a remote lamp and an off-axis view port.

FIG. 2A illustrates an embodiment of the invention having a remote lamphouse s containing a standard 150 watt reflector-type projection lamp 9 to focus light rays onto a fiber optical cable 10. The intensity of the lamp 9 can be controlled with a rheostat. The lamphouse 8 is of the type of commercially available light source commonly used for fiber optics illumination. The fiber optical cable may be a commercially available, flexible fiber optics lightguide which is a bundle of glass fibers arranged into a light conduit one-fourth to one-half inches in diameter. A typical length for the cable 10 is from one to two meters.

The output radiation from the lamp 9 is not limited to the visible spectrum. Through the use of appropriate filters or lamps 9, ultraviolet light or infrared light may be supplied via the fiber optical cable 10.

The fiber optical cable 10 is connected to a removable reflector housing top 11 constructed of machined aluminum. The reflector housing top 11 provides a receptacle for terminating the fiber optical cable 10.

As shown in FIG. 2A, the light rays 12 emitted from the fiber optical cable 10 diverge due to the numerical aperture function of the Fiber optical cable 10. The light rays 12 are incident upon a negative beam diverging lens 13, which causes the light rays to diverge in preparation for illuminating the hemispherical diffuser 14. The lens 13 is an achromatic negative lens with a minus forty-four millimeter effective focal length. The diverging lens 13 is used to shape and direct the incident light rays 12 to produce exit light rays 15 which are incident upon the hemispherical diffuser 14 and the interior walls 16 of the conical reflector 17. The diverging lens is required to providing the correctly angled rays 15 for a uniform distribution of light across the convex surface 18 of the hemispherical diffuser 14. The diverging lens 13 form factor, size and focal length can be varied to match the application.

The conical reflector 17 which is attached to the reflector housing top 11, is constructed of machined aluminum and serves to reflect the exit light rays 15 to obtain uniform illumination of the lower portions of the convex surface 18 of the diffuser 14. The interior walls 16 of the conical reflector 17 are critically angled and polished to reflect the exit light rays 15 to the correct areas of the convex surface 18 of the diffuser. The separation of the walls 16 also is critical to correct light reflection.

The hemispherical diffuser 14 is a hollow hemisphere made from thin walled plastic or any other translucent material having optical "milk glass" diffusing characteristics. Examples are twenty to thirty mil thick lexan, polypropylene, or molded glass. The diffusing characteristics can be inherent in the optical medium of the translucent material of the diffuser, such as "milk glass" or a clouding aspect, and/or the diffusing characteristics can be provided by texturing the convex surface 18 and/or the concave surface 19 of the hemispherical diffuser 14. The texturing can be done by sandblasting or etching the convex and/or concave surfaces.

The object 20 under illumination is located approximately at the center of curvature of the concave surface 19. Typically, the working distance from the object 20 under illumination to the lower edge of the hemispherical diffuser 14, ranges from 0.0625 inches for smaller diffusers, having diameters of approximately 1.5 inches and used for purposes such as solder joint inspection, to several inches for larger diffusers with diameters of twelve inches or larger.

The diffuser emanates light uniformly from the concave surface 19 which subtends a solid angle of approximately two-pi steradians (180 degree solid angle) measured at the upper surface of the object 20 illuminated. Thus, the surface of the object 20 sees a uniform distribution of light coming from the entire concave surface 19. Thus, shadowless illumination of the surface of the object 20 is achieved. This feature eliminates bright specular reflections, as the uniformity and diffusivity of the illumination is much greater than with conventional illumination systems. Video cameras can safely be used without danger of blooming, saturation and video overloads. Therefore, video cameras can now be used for applications previously impossible. Highly reflective objects are visible in their entirety, using video cameras or conventional photography.

The object 20 under illumination may virtually be any type or shape of object that normally is observable with visible, UV or IR wavelengths of radiation. In the electronics field, solder joints may be inspected.

Figure 2B:
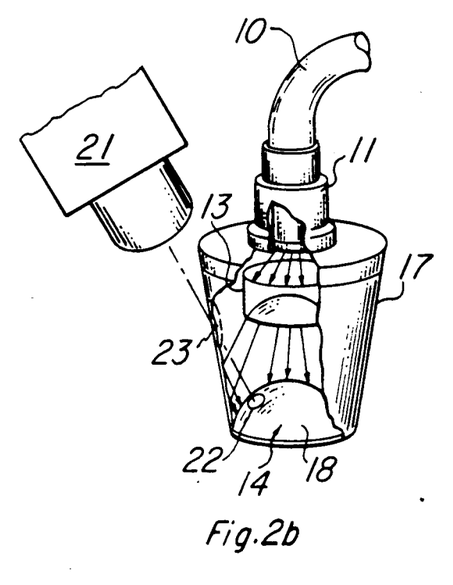
FIG. 2B is a perspective view of the embodiment of the invention shown in FIG. 2A.

FIGS. 2A and 2B show video camera 21 viewing the object 20 through the off-axis viewing port 22 in the diffuser 14 and the off-axis viewing port 23 in the conical reflector 17.

The video camera 21 may be a tube-type or CCD device. Instead of a video camera, the viewing device may be a still or movie camera, a microscope or other optical magnifier with the same improvements in image quality.

Figure 3A:
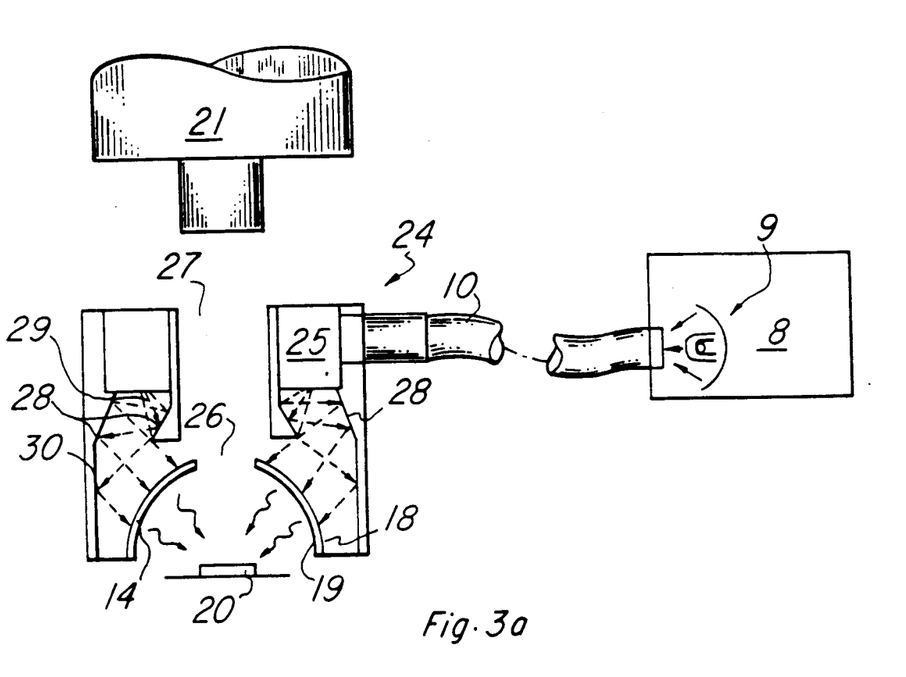
FIG. 3A is a side sectional view of an embodiment of the invention with a remote lamp and an axially located view port.
Figure 3B:
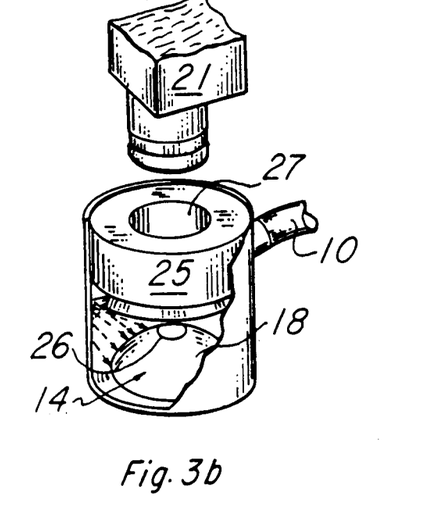
FIG. 3B is a perspective view of the embodiment of the invention shown in FIG. 3A.

FIGS. 3A and 3B show an on-axis view port embodiment of the invention. In this embodiment, the components are similar to those in the off-axis viewing port embodiment illustrated in FIGS. 2A and 2B. With this embodiment, viewing of the object 20 is accomplished through the center of the illuminator 24 instead of at an angle from a normal to the observed object 20. Viewing takes place through the viewing port 26 in the diffuser 14 and the viewing port 27 in the fiber optics ring. This embodiment is useful for use as a microscope illuminator for human observation, as well as television or video monitoring.

The remote lamphouse 8 and the fiber optical cable 10 are as shown in FIG. 2A. The Fiber optical cable 10 terminates in a fiber optics ring 25, which is obtainable commercially. The Fiber optical cable 10 used in the on-axis embodiment terminates into a fiber optics ring 25 which is an annulus of light emitting fibers. Typical sizes are two inch to four inch diameters with an annulus width of 0.020 to 0.050 inches. The fibers are arranged to converge the light from the annulus to produce a smooth, uniform distribution of light at a predetermined working distance. A typical working distance for commercially available fiber optics rings is 1.5 inches, and provides uniform illumination over a one inch diameter spot.

The fiber optics ring 25 directs light rays 29 to be incident upon the convex surface 18 of the diffuser 14, and against concical reflectors 28 and 30 which direct the reflected light rays to illuminate the lower areas of the convex surface 18.

The diffuser 14 is as described in connection with FIG. 2A, except for the location of the viewing ports.

Figure 4A:
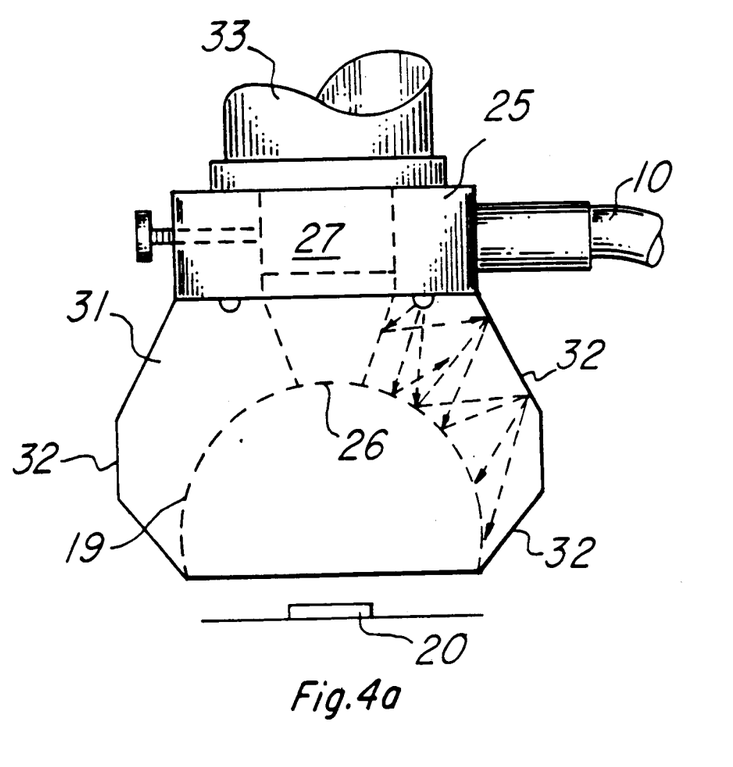
FIG. 4A is a side sectional view of an embodiment of the invention with a remote lamp and a flat diffuser surface opposite the convex surface.
Figure 4B:
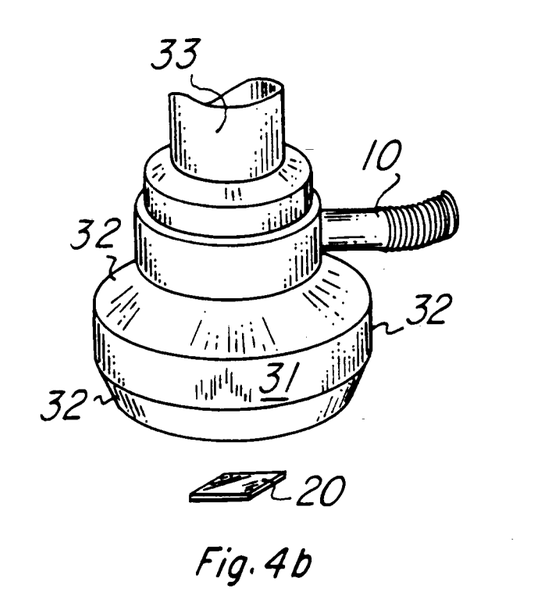
FIG. 4B is a perspective view of the embodiment of the invention shown in FIG. 4A.
Figure 5A:
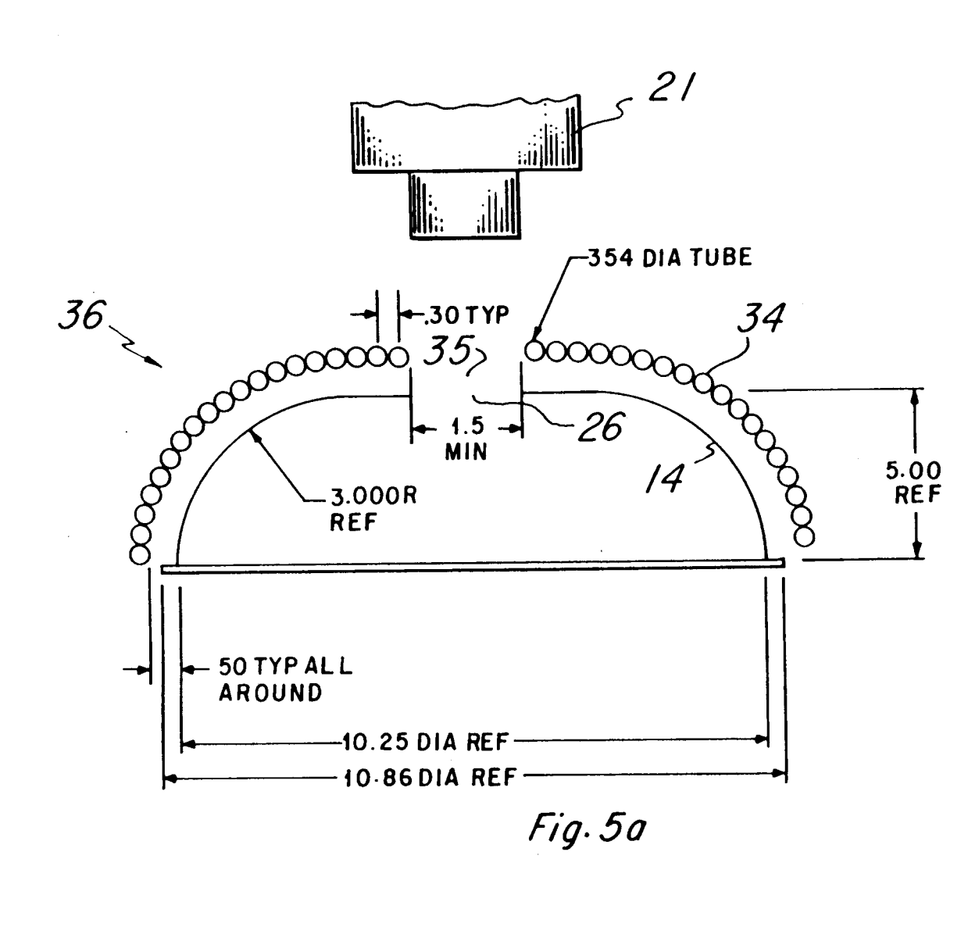
FIG. 5A is a side sectional view of an embodiment of the invention with a flattened, hemispherically shaped spiral lamp covering the diffuser.
Figure 5B:
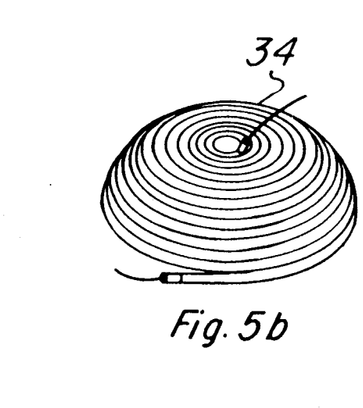
FIG. 5B is a perspective view of the embodiment of the invention shown in FIG. 5A.

FIGS. 4A and 4B illustrate an embodiment of the invention having a one-piece, diffuser assembly 31 machined from a solid piece of acrylic plastic. Alternatively, instead of machining, the diffuser assembly may be molded into its final form. Also, instead of being a single piece, it may be made of or divided into several component pieces. This embodiment of the invention is an on-axis design having an on-axis viewing port 26 in the diffuser assembly 31, and an on-axis viewing port 27 in the fiber optics ring 25. The hemispherical concave surface 19 may be sandblasted, etched, molded or otherwise treated to acquire a diffusing texture. Alternatively, or in addition, a thin milk glass plastic insert can be placed between the fiber optics ring 25 and the diffuser assembly 31 to achieve the desired diffusing characteristics. Reflecting surfaces 32 are critically angled to achieve internal reflection of incident light from the fiber optics ring 25, and to direct the reflected light toward the lower areas of the hemispherical concave surface 19, to achieve uniform illumination of the concave surface 19. The reflecting surfaces 32 may be silvered to increase the intensity of the reflected light.

This embodiment can be attached directly to a conventional microscope in much the same manner as commercially available fiber optics ring illuminators. The objective lens 33 of such a microscope is shown as being disposed directly above the fiber optics ring 25. This embodiment can be molded from plastic compounds as a low cost illumination accessory for a broad range of microscopic applications.

FIGS. 5A, 5B, 6A and 6B illustrate two similar embodiments of the invention having on-axis viewing ports. Each of these embodiments includes a locally located, spirally wound lamp 34 for providing a source of very uniform light distribution to the hemispherical diffuser 14. The locally located, spirally wound lamp 34 replaces the remotely located lamp, fiber optical cable 10, fiber optics ring 25, diverging lens 13 and various reflectors of the previously described embodiments. The spirally wound lamp is constructed from nine millimeter diameter pyrex glass tubing filled with neon. The glass tubing can be wound in one complete spiral, or be constructed of separate segments. Typically, this lamp is energized with nine kilovolts at forty-five milliamps. The resultant emittance is categorized as "bright white" in color temperature, and is considerably brighter than standard fluorescents. This type of lamp can be made in virtually any size, from 1.5 inches in diameter to more than twelve inches.

An on-axis viewing port 26 is provided in diffuser 14, and a corresponding on-axis viewing port 35 is provided in the center of the spirally wound lamp. The embodiment of FIGS. 5A and 5B differ from the embodiment of FIGS. 6A and 6B in that the hemispherical shape of the spiral lamp 34 and diffuser 14 is somewhat flattened in the embodiment of FIGS. 5A and 5B, but has a true hemispherical shape in FIGS. 6A and 6B. The flattened shape provides for a lower profile illuminator 36, allowing the illuminator 36 to be used in more cramped situations.

Figure 6A:
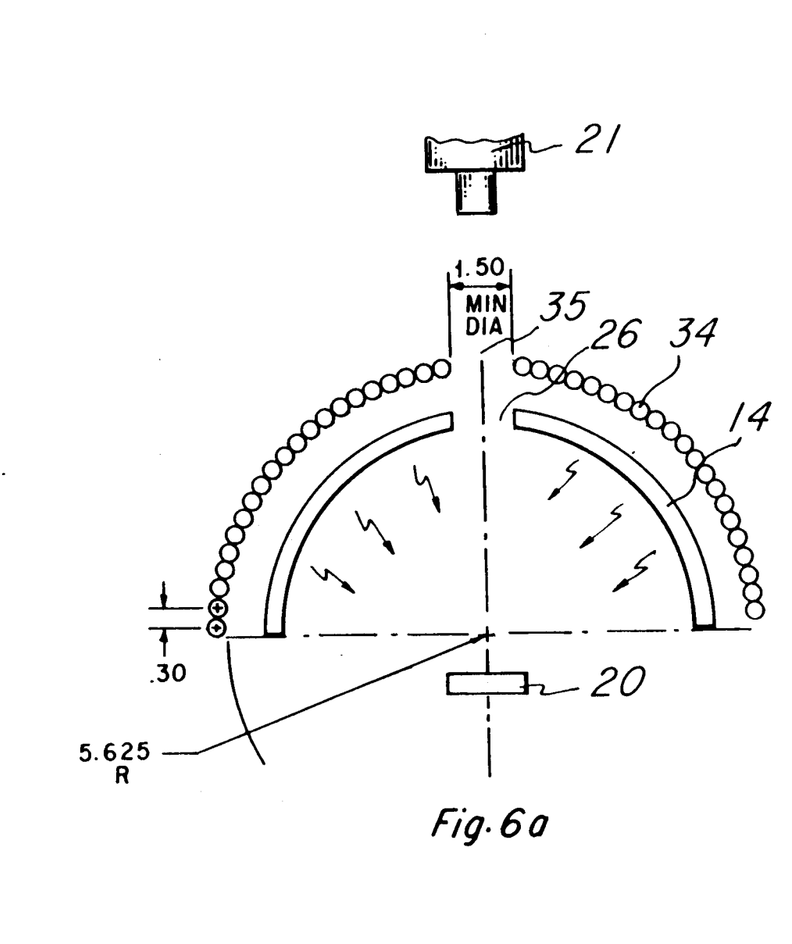
FIG. 6A is a side sectional view of an embodiment of the invention with a hemsipherically shaped spiral lamp covering the diffuser.
Figure 6B:
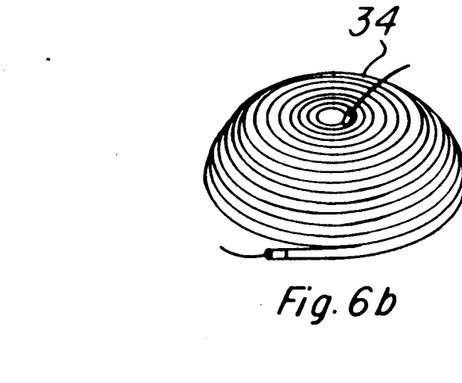
FIG. 6B is a perspective view of the embodiment of the invention shown in FIG. 6A.
Figure 7A:
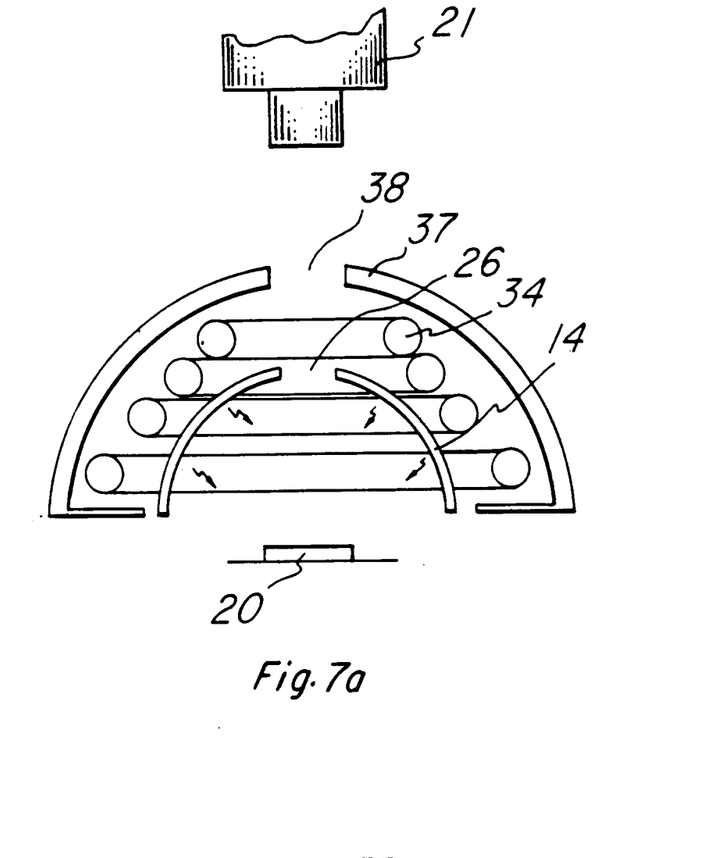
FIG. 7A is a side sectional view of an embodiment of the invention with a hemispherically shaped reflector covering a hemsipherically shaped spiral lamp which, in turn, covers the diffuser.
Figure 7B:
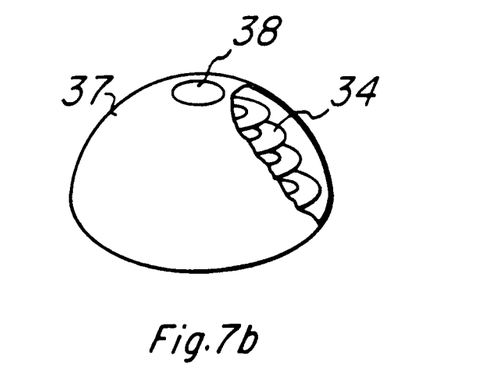
FIG. 7B is a perspective view of the embodiment of the invention shown in FIG. 7A.

FIGS. 7A and 7B illustrate an embodiment like that of FIGS. 6A and 6B, with the addition of a hemispherical reflector 37 having an on-axis viewing port 38 in the center of the reflector 37.

Figure 8:
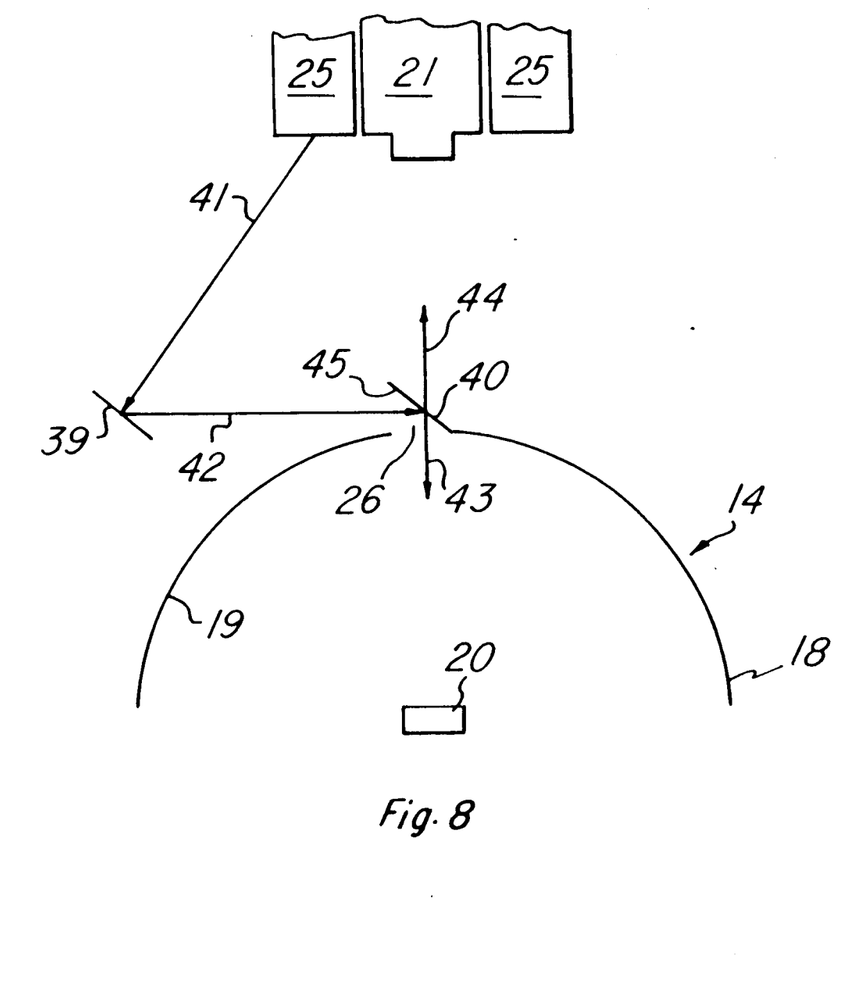
FIG. 8 is a side sectional view of an embodiment of the invention with a beam splitter or half-silvered mirror.

The various illustrated embodiments of the invention include viewing ports in the diffuser 14 or diffuser assembly 31. For certain applications involving extremely specularly reflective surfaces, the relatively dark area associated with the viewing port 26 in the diffuser 14 may cause an image of the dark area to be reflected from the object 20 and to be picked up by video camera 21. This image of the dark area can, in certain instances, obscure or mask small features or detail in the surface of the object 20. In FIG. 8, a beam splitter 40, or half-silvered mirror, is placed over the viewing port 26, at a forty-five degree angle. Light rays 41 from fiber optics ring 25 are reflected from reflecting surface 39, and the reflected light rays 42 are directed to be incident upon the surface 45 of the beam splitter 40. The light rays 42 are reflected from the surface 45, and the reflected light rays 43 are directed axially toward the illuminated object 20. Most of the light rays incident upon the beam splitter 40 which have been reflected by the object 20, pass through the beam splitter as light rays 44 and are detected by the video camera 21. Thus, the object 20 is bathed in a uniform light distribution originating from all angles subtended by the diffuser 14, and the viewing port 26 appears to be invisible to the camera. For this embodiment to function most efficiently, the light from the fiber optics ring should be of high intensity. The beam splitter can be used with the various other embodiments of the invention, although it is not normally necessary for most inspection or viewing applications.

I claim:

1. A diffuser assembly for shadowless illumination of an object comprising:
   a translucent diffuser having a substantially hemispherical, concave surface;
   a diverging lens spaced from, shaping and directing light onto said diffuser
   a light source positioned to direct light rays through said diverging lens and into the optical medium of said diffuser;
   wherein substantially all of the light rays incident at the center of the curvature of the concave surface pass through the translucent diffuser.

2. The diffuser assembly of claim 1, wherein said light source comprises:
   a lamp remote from said diffuser; and
   a fiber optical cable for conducting light from said lamp to said position to direct light into the optical medium of said diffuser.

3. The diffuser assembly of claim 1, further comprising:
   at least one reflector for reflecting light into the optical medium of said diffuser.

4. The diffuser assembly of claim 1, wherein:
   the optical medium of said diffuser has a milk glass optical consistency to diffuse light.

5. The diffuser assembly of claim 1, wherein:
   said concave surface is textured to scatter light.

6. The diffuser assembly of claim 5, wherein:
   said concave surface is a sandblasted surface.

7. The diffuser assembly of claim 5, wherein:
   said concave surface is an etched surface.

8. The diffuser assembly of claim 1, wherein:
   said diffuser is plastic.

9. The diffuser assembly of claim 1, wherein: said diffuser is glass.

10. The diffuser assembly of claim 1, wherein said diffuser further comprises:
a convex surface positioned to receive said directed light from said light source.

11. The diffuser assembly of claim 10, wherein:
said convex surface is textured to scatter said directed light as it enters the optical medium of said diffuser.

12. The diffuser assembly of claim 1, further comprising:
a viewing port located in said diffuser.

13. The diffuser assembly of claim 1, wherein the diffuser assembly is symmetrical about an axis, further comprising:
a viewing port off-axially located in said diffuser.

14. A method of shadowless illumination of an object, comprising the steps:
(a) providing a translucent diffuser having a substantially hemispherical, concave surface;
(b) positioning an object to be illuminated near the center of curvature of said concave surface; and
(c) directing substantially all light rays through a lens spaced from said diffuser to uniformly distribute the light rays into the optical medium of said diffuser, in a direction to cause light to be radiated uniformly from said concave surface toward said object, to illuminate said object.

15. The method of claim 14, wherein step (b) includes the step:
positioning said object to be illuminated, below the bottom edge of said concave surface.

16. The method of claim 14, wherein step (c) includes the step:
providing reflectors positioned to reflect light into the optical medium of said diffuser.

17. The method of claim 14, wherein step (a) includes the step:
providing a viewing port in said translucent diffuser.

18. The method of claim 17, further comprising the step:
(d) viewing the illuminated object through said viewing port.

19. The method of claim 18, wherein step (d) includes the step:
viewing said object through said viewing port with a video camera.

20. The method of claim 18, wherein step (d) includes the step:
viewing said object through said viewing port with a microscope.

21. The method of claim 17, further comprising the step:
(d) providing a means for directing light through said viewing port toward said object to prevent an image of said viewing port from being reflected from said object.

22. The method of claim 21, wherein:
said directing means include means for passing light reflected from said object.

23. A diffuser assembly for shadowless illumination of an object, comprising:
a translucent diffuser having a substantially hemispherical, concave surface;
a light source for directing light rays into the optical medium of said diffuser;
a lens positioned between and spaced from the light source and the diffuser for uniformly distributing the light rays on to the diffuser;
a viewing port in said diffuser for viewing an object positioned near the center of curvature of said concave surface; and
a means for directing light through said viewing port toward said object, and for passing light reflected from said object;
wherein substantially all of the light rays incident at the center of the curvature of the concave surface pass through the translucent diffuser.

24. The diffuser assembly of claim 23, wherein:
said means is a beam splitter.

25. The diffuser assembly of claim 23, wherein:
said means is a half-silvered mirror.

26. The diffuser assembly of claim 23, wherein:
said means includes a reflecting surface positioned to reflect light through said viewing port toward said object.

* * * * *